United States Patent [19]

Gaffar et al.

[11] Patent Number: 5,158,763

[45] Date of Patent: * Oct. 27, 1992

[54] NON-STAINING ANTI-BACTERIAL ORAL COMPOSITION

[75] Inventors: Abdul Gaffar, Princeton; Thomas G. Polefka, Somerset, both of N.J.

[73] Assignee: Colgate-Palmolive Company, Piscataway, N.J.

[*] Notice: The portion of the term of this patent subsequent to Mar. 17, 2009 has been disclaimed.

[21] Appl. No.: 594,598

[22] Filed: Oct. 9, 1990

[51] Int. Cl.$^5$ .......................... A61K 7/16; A61K 7/22
[52] U.S. Cl. ........................................ 424/54; 424/49
[58] Field of Search .................................. 424/49-58

[56] References Cited

U.S. PATENT DOCUMENTS

| | | | |
|---|---|---|---|
| Re. 32,300 | 12/1986 | Gorman et al. | 514/635 |
| 3,934,002 | 1/1976 | Haefele | 424/54 |
| 3,937,805 | 2/1976 | Harrison | 424/54 |
| 3,937,807 | 2/1976 | Haefele | 424/54 |
| 3,941,772 | 3/1976 | Ploger et al. | 424/54 |
| 3,984,543 | 10/1976 | Ploger et al. | 424/54 |
| 4,025,616 | 5/1977 | Haefele | 424/54 |
| 4,034,086 | 7/1977 | Ploger et al. | 424/57 |
| 4,042,679 | 8/1977 | Gaffar | 424/54 |
| 4,051,234 | 9/1977 | Gieske et al. | 424/54 |
| 4,054,598 | 10/1977 | Blum et al. | 424/54 |
| 4,059,624 | 11/1977 | Harrison | 424/54 |
| 4,064,164 | 12/1977 | Blum et al. | 424/54 |
| 4,108,961 | 8/1978 | Ploger et al. | 424/57 |
| 4,108,962 | 8/1978 | Ploger et al. | 424/57 |
| 4,117,086 | 9/1978 | Ploger | 424/57 |
| 4,117,090 | 9/1978 | Ploger | 424/57 |
| 4,118,472 | 10/1978 | Gaffar et al. | 424/57 |
| 4,118,473 | 10/1978 | Gaffar et al. | 424/57 |
| 4,118,474 | 10/1978 | Gaffar et al. | 424/57 |
| 4,118,475 | 10/1978 | Gaffar et al. | 424/57 |
| 4,118,476 | 10/1978 | Gaffar et al. | 424/57 |
| 4,122,151 | 10/1978 | Ploger | 424/57 |
| 4,123,512 | 10/1978 | Gaffar | 424/57 |
| 4,130,630 | 12/1978 | Ploger et al. | 424/57 |
| 4,130,637 | 12/1978 | Bauman | 424/54 |
| 4,420,484 | 12/1983 | Gorman et al. | 514/332 |
| 4,882,359 | 11/1989 | Nakagawa et al. | 514/947 |

FOREIGN PATENT DOCUMENTS 2442712  3/1976  Fed. Rep. of Germany ........ 424/54

OTHER PUBLICATIONS

Nowak, C.A. 69:99294h (1968).
L'Orange et al., C.A. 84:184919v (1976) of Ger. Offen. 2,442,712, Mar. 25, 1976.
Sugiyama et al. C.A. 111:140243s (1989) of JP 63211217, Sep. 2, 1988.

Primary Examiner—Shep K. Rose
Attorney, Agent, or Firm—Paul Shapiro; Robert C. Sullivan

[57] ABSTRACT

An oral composition is provided which comprises an oral vehicle and contains at least one antibacterial antiplaque agent which can stain or discolor dental surfaces. Provided in such oral composition is an effective stain-inhibiting amount of an antistaining additive, such additive being azacycloalkane disphosphonic acid or an orally acceptable salt thereof.

16 Claims, No Drawings

NON-STAINING ANTI-BACTERIAL ORAL COMPOSITION

BACKGROUND OF THE INVENTION

This invention relates to an antibacterial oral composition which promotes oral hygiene and in particular is directed to such oral composition which comprises a cationic nitrogen-containing antibacterial agent incorporated therein to prevent plaque formation caused by bacteria in the oral cavity.

As is described in more detail herein, such compositions have employed a wide range of antibacterial compounds such as quaternary ammonium compounds and substituted guanidines. Many of these compounds have been shown to effectively promote oral hygiene and, in particular, inhibit plaque formation. Unfortunately, however, it has been observed that the use of such oral compositions has led to the staining or discoloration of dental surfaces.

The reason for the formation of such dental stain has not been clearly established. It is believed however that stain results from the entrapment of stain chromophores in dental calculus. Cationic antimicrobials enhance the staining process by accelerating both the formation of the stain chromophores and the deposition of calculus. This phenonomon is described in A. Gaffar, et al., Journal of Dental Research, Vol. 60, No. 8, pp. 1432–1439 (August 1981).

The art has long sought to employ additives which reduce the dental staining properties of antibacterial agents. Thus, for example, in U.S. Pat. No. 3,934,002 to Haefele the staining properties of bis-biguanide compounds are sought to be inhibited by the inclusion of such compounds as zinc phenol sulfonates hydroxy quinoline, homopolymers and copolymers of aliphatic polycarboxylic acids, certain polyphosphates, certain salts of rare earth metals, phytic acid and certain polyphosphonates and ammonium polyphosphonates. In U.S. Pat. No. 4,042,679 to Gaffar the staining properties of bis-biguanido hexanes and quaternary ammonium salts such as benzethonium chloride and cetyl pyridinium chloride are said to be inhibited by employing as an antistain additive, a polymeric polyphosphonic compound such as polyalkyl bis-(phosphonomethylene) amine acid. In U.S. Pat. No. 4,224,309 to Gaffar, et. al., the antistaining properties of such bis-biguanido hexanes and quaternary ammonium salts are said to be inhibited by employing as an antistain additive a 2-phosphono-butane-1,2,4-tricarboxylic acid compound. In U.S. Pat. No. 4,118,474 to Gaffar, et al, the antistaining properties of such antibacterial agents are said to be inhibited by employing as an antistain additive phosphonoacetic acid and its salts.

For one reason or another, these prior suggestions have not proven to be widely used. For example, previously employed additives which reduced dental staining by cationic antibacterial antiplaque agents also generally reduced their antibacterial and antiplaque activities as by forming a precipitate with such agents.

Accordingly, it is desirable to employ, together with a cationic antibacterial agent, an antistaining additive which does not decrease the antibacterial, antiplaque activity of the antibacterial agent and thus far, a completely satisfactory additive has eluded the art.

SUMMARY OF THE INVENTION

In accordance with the teachings herein, it has been discovered that an additive may be provided in an oral composition comprising a cationic nitrogen containing antibacterial agent which additive will inhibit the staining of said agent without inhibiting the antibacterial, antiplaque activity of said agent. Specifically, an oral composition is provided comprising an oral vehicle and at least one nitrogen containing, cationic antibacterial, antiplaque agent which agent has been observed to have dental surface staining activity. In accordance with this invention, said composition further comprises, as an antistaining additive an effective stain-inhibiting amount of an azacycloalkane diphosphonic acid or an orally acceptable salt thereof.

The azacycloalkane should be present in a quantity sufficient to provide antistaining properties but insufficient to cause precipitation of the antibacterial agent. Generally, for example, the concentration of the antibacterial agent in the oral composition will range from about 0.05 to about 1.0% by weight of the oral composition. In such case, the antistaining additive of this invention should range from about 0.1 to about 5.0% by weight. Preferably, the antistain additive is present in a quantity of about two to about ten times the quantity of the antibacterial agent, by weight. The azacycloalkane of choice is azacycloheptane diphosphonic acid and salts thereof.

DETAILED DESCRIPTION OF THE INVENTION

The antistaining additive of the oral composition of this invention is an azacycloalkene-2,2-diphosphonic acid of the general formula

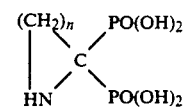

in which n is an integer of from 3 to 5, or a water-soluble salt thereof. As is taught in U.S. Pat. No. 3,941,772 to Ploger, the additives may be produced by reacting a lactum of the formula

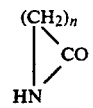

in which n represents an integer of from 3 to 5, with phosphorus trihalides or mixtures of phosphorus trihalides and phosphoric acid, hyrolyzing the reaction product and, if desired, converting into the salts. The reaction is generally effected at temperatures of from 40° to 150° C. Suitable starting substances are for example, pyrrolidone (n=3), piperidone (n=4) and caprolactam (n=5) which are readily available as commercial products. The later starting substance, caprolactan will result in the preferred azacycloheptane diphosphoric acid or salt. The reaction may be carried out, for example, by first melting the lactam with phosphorous acid and slowly adding PCl$_3$ with stirring. The mostly viscous reaction product formed is then hydrolyzed by addition of water. The molten lactam can also be reacted directly with phosphorus trihalides and hydrolyzed in stages. Suitable phosphorus trihalides are phosphorus trichloride and phosphorus tribromide. The preferred molar ratios of lactum to phosphorus compound ranges from 1:2 to 1:6. Hydrolysis is affected by the addition of water to the reaction mixture or in the presence of alkali e.g., caustic soda or caustic potash.

Suitable water soluble salts of the azacycloalkane diphosphonic acid stain inhibiting additive of this invention are, for example, alkali metal salts e.g., lithium, sodium or potassium salts and ammonium salts. The acid may be converted to the desired salt by neutralization with the appropriate base.

The antistaining azacycloalkane diphosphonic acid or salt thereof additives should be present in the oral composition of this invention in a quantity, by weight, of from about 0.1 to about 10 times the weight of the antibacterial agent e.g., from about 0.001 to about 10% by weight of the oral composition. Preferably the antistaining additive is present in a quantity, by weight, of from about 1.0 to about 10 times the weight of the antibacterial agent or from about 0.01 to about 5% by weight of the oral composition.

The antibacterial agent employed in accordance with this invention may be any of the well known cationic antibacterial agents which are known to have dental surface staining characteristics and which may be classified as the bis-biguanide alkanes and the quaternary ammonium salts antibacterial antiplaque agents.

Such bis-biguanides are described in German patent application No. P2,332,383 published on Jan. 10, 1974 and having the generic formula

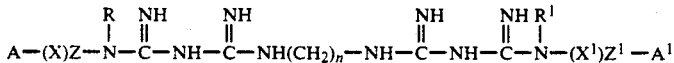

wherein A and $A^1$ each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and $X^1$ each represent an alkylene radical containing from 1 to 3 carbon atoms; wherein Z and $Z^1$ each can be either 0 or 1; wherein R and $R^1$ each represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms, aromatic nuclei, etc. Usable water soluble salts of the above are chloride, bromides, sulfates, alkyl sulfonates such as methyl sulfonate and ethyl sulfonate, phenylsulfonates such as p-methylphenyl sulfonates, nitrates, ocetates, gluconates, etc.

Examples of suitable bis biguanide compounds are 1,6-bis-(2-ethylhexylbiguanidohexane)dihydrochloride; 1,6-di-($N_1$, $N_1'$-phenyldiguanido-$N_5$, $N_5'$)-hexane tetrahydrochloride; 1,6-di-($N_1$, $N_1'$-phenyl-$N_1$, $N_1'$-methyldiguanido-$N_5$, $N_5'$)-hexane dihydrochloride; 1,6-di($N_1$, $N_1'$-o-chlorophenyldiguanido-$N_5$, $N_5'$)-hexane dihydrochloride; 1,6-di($N_1$, $N_1'$-2,6-dichlorophenyldiguanido-$N_5$, $N_5'$)hexane dihydrochloride; 1,6-di[$N_1$, $N_1'$-$\beta$-(p-methoxyphenyl) diguanido-$N_5$, $N_5'$]-hexane dihydrochloride; 1,6-di($N_1$, $N_1'$-$\alpha$-methyl-$\beta$-phenyldiguanido-$N_5$, $N_5'$)-hexane dihydrochloride; 1,6-di($N_1$, $N_1'$-p-nitrophenyldiguanido-$N_5$, $N_5'$)hexane dihydrochloride;$\omega$:$\omega'$-di-($N_1$, $N_1'$-phenyldiguanido-$N_5$, $N_5'$)-di-n-propylether dihydrochloride;$\omega$:$\omega'$-di($N_1$, $N_1'$-p-chlorophenyldiguanido-$N_5$, $N_5'$)-di-n-propylether tetrahydrochloride; 1,6-di($N_1$, $N_1'$-2,4-dichlorophenyldiguanido-$N_5$, $N_5'$)hexane tetrahydrochloride; 1,6-di($N_1$, $N_1'$-p-methylphenyldiguanido-$N_5$, $N_5'$)hexane dihydrochloride; 1,6-di($N_1$, $N_1'$-2,4,5-trichlorophenyldiguanido-$N_5$, $N_5'$)hexane tetrahydrochloride; 1,6-di[$N_1$, $N_1'$-$\alpha$-(p-chlorophenyl) ethyldiguanido-$N_5$, $N_5'$] hexane dihydrochloride;$\omega$:$\omega'$di($N_1$, $N_1'$-p-chlorophenyldiguanido-$N_5$, $N_5'$)m-xylene dihydrochloride; 1,12-di($N_1$, $N_1'$-p-chlorophenyldiguanido-$N_5$, $N_5'$) dodecane dihydrochloride; 1,10-di($N_1$, $N_1'$-phenyldiguanido-$N_5$, $N_5'$)-decane tetrahydrochloride; 1,12-di($N_1$, $N_1'$-phenyldiguanido-$N_5$, $N_5'$) dodecane tetrahydrochloride; 1,6-di($N_1$, $N_1'$-o-chlorophenyldiguanido-$N_5$, $N_5'$) hexane dihydrochloride; 1,6-di($N_1$, $N_1'$-p-chlorophenyldiguanido-$N_5$, $N_5'$)-hexane tetrahydrochloride; ethylene bis (1-tolyl biguanide); ethylene bis (p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenyl biguanide); trimethylene bis(o-tolyl biguanide); N-butyl trimethylene bis(phenyl biguanide); tetramethylene bis(1-tolyl biguanide); the specific compounds disclosed in U.S. Pat. No. 2,863,919, Birtwell et. al., (Dec. 9, 1958), said patent being incorporated herein by reference; the specific compounds disclosed in U.S. Pat. No. 3,468,898, Cutler et. al., (Sep. 23, 1969), said patent being incorporated herein by reference; and the corresponding pharmaceutically acceptable salts of all of the above such as the acetates; gluconates; hydrochlorides; hydrobromides; citrates; bisulfites; fluorides; polymaleates; N-coconutalkyl sarcosinates; phosphites; hypophosphites; perfluorooctanoates; silicates; sorbates; salicylates; maleates; tartrates; fumarates; ethylenediaminotetraacetates; iminodiacetates; cinnamates; thiocyanates; arginates; pyromellitates; tetracarboxybutyrates; benzoates; glutarates; monofluorophosphates; and perfluoropropionates.

The bis biguanide of choice is chlorhexidine digluconate.

Usuable also as the antibacterial, antiplaque agent in the oral composition of this invention are the antibacterial quaternary ammonium components such as are described under the section on "Quaternary Ammonium and Related Compounds" in the article on Antiseptic and Disinfectants" in Kirk-Othmer Encyclopedia of Chemical Technology, second edition (Vol. 2, p. 632–635), incorporated herein by reference. Among the most common of these antibacterial, antiplaque quaternary ammonium compounds is benzethonium chloride (Hyamine 1622 or diisobutyl phenoxyethoxyethyl dimethyl benzyl ammonium chloride). In an oral preparation, this material is highly effective in promoting oral hygiene by reducing dental plaque. Agents of this type are described in U.S. Pat. Nos. 2,984,639; 3,328,402; 3,431,208; 3,703,583 and in British Patent No. 1,319,396.

In general, usable quarternary ammonium compounds include those in which one or two of the substituents on the quaternary nitrogen have a carbon chain length, typically as an alkyl group, of some 8 to 20 carbon atoms e.g., 10 to 18 carbon atoms while the remaining substituents have a lesser number of carbon atoms, typically as alkyl or benzyl group, such as 1 to 7 carbon atoms e.g., methyl or ethyl group. In addition to the benzethonium chloride agent described above, exemplary quaternary nitrogen compounds are benzalkonium chloride, cetalkonium chloride, cetalkonium bromide, cetylpyridinium, coco-amidopropyldimonium hydroxypropylamino hydrolyzed animal protein, domiphen bromide, lauralkonium bromide, lauralkonium chloride, lauraminopropyl acetamidodimonium chloride, laurylpropyridinium chloride and others.

Expressly excluded are those quaternary ammonium compounds or complexes which are not antibacterial. For example in U.S. Pat. No. 4,820,507 issued to Hans-Juergen Klueppel et al, a polyhydric quaternary ammonium cationic complexed to an organophosphoric amine is illustrated as having antiplaque and non staining characteristics. This compound, however, is said to be substantially nonantimicrobial and hence is excluded the term "antibacterial agent" as used herein. Most probably, the antiplaque nature of the compound results from its surface active characteristics rather than the subject of this invention, i.e. antibacterial activity.

The antibacterial antiplaque compound is preferably one which has an antibacterial activity such that its phenol co-efficient is well over 50, more preferably well above 100, such as above about 200 or more for S, aureus; for instance the phenol coefficient (A.O.A.C.) of benzethonium chloride is given by the manufacturer as 410, for S. aureus. The cationic antibacterial agent will generally be a monomeric (or possibly dimeric) material of molecular weight well below 2,000, such as less than about 1,000. It is, however, within the broader scope of the invention to employ a polymeric cationic antibacterial agent. The cationic antibacterial is preferably supplied in the form of an orally acceptable salt thereof, such as the chloride, bromide, sulfate, alkyl sulfonate such as methyl sulfonate and ethyl sulfonate, phenylsulfonate, such as p-methylphenyl sulfonate, nitrate, acetate, gluconate, etc.

The antibacterial antiplaque agents should be present in the oral composition of this invention in the quantity of from about 0.01 to about 5% by weight of the oral composition and preferably from about 0.01 to about 3% by weight of the oral composition. The antibacterial antiplaque agent of choice is chlorhexidine (1,1'-hexamethylene-bis [5-(4-chlorophenyl)-biquanide]) and still more preferably chlorhexidine gluconate.

In certain highly preferred forms of the invention, the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zironium silicates, bentonite, and mixtures thereof. Preferred polishing materials include complex amorphorus alkali metal aluminosilicate and hydrated alumina.

Alumina, particularly the hydrated alumina sold by Alcoa as C333, which has an alumina content of 64.9% by weight, a silica content of 0.008%, a ferric oxide content of 0.003%, and a moisture content of 0.37%, at 100° C., and which has a specific gravity of 2.42 and a particle size such that 100% of the particles are less than 50 microns and 84% of the particles are less than 20 microns, is particularly desirable.

When visually clear gels are employed, polishing agents comprising alkali metal aluminosilicate complexes are particularly useful, since they have refractive indices close to the refractive indices of gelling agent-liquid (including water and/or humectant) systems commonly used in dentifrices.

Many of the so-called "water-soluble" polishing materials are anionic in character and also include small amounts of soluble material. Thus, insoluble sodium metaphosphate may be formed in any suitable manner, as illustrated in Thorpe's Dictionary of Applied Chemistry, Volume 9, Fourth Edition, pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 20 to about 99% by weight of the oral preparation. Preferably, it is present in amounts ranging from about 20 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antibacterial antiplaque agent and additive should be compatible with the other components of the preparation. Thus, in a toothpaste, the liquid vehicle may comprise water and humectant typically in an amount ranging from about 10 to about 90% by weight of the preparation. Glycerine, sorbitol, xylitol or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3-30% by weight of water, 0 to about 80% by weight of glycerine, and about 20-80% by weight of sorbitol is preferably employed. A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch, or preferably hydroxypropyl methyl cellulose or the Carbopols (e.g., 934,940 and 941) or the like is usually present in toothpaste in an amount up to about 10% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

In oral compositions such as mouthrinses and toothpastes, a surfactant is often present, e.g. to promote foaming. It will be understood that it is preferable to employ nonionic or amphotenic surfactants rather than their anionic counterparts. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of ethylene oxide with fatty acids, fatty alcohols and fatty amides including alcohols such as sorbitan monostearate or polypropyleneoxide (that is Pluronic materials).

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type or oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 to 0.05%, by weight, of fluoride ion.

Various other materials may be incorporated in the oral preparations of this invention. Examples are whitening agents, preservative, silicones, chlorophyl compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, APM (aspartyl phenylalanine, methylester), and saccharine. Suitably, flavor and sweetening agents may together comprise from about 0.1 to 5% or more of the preparation.

In preparing the oral compositions of this invention comprising the above-defined combination of antibacterial agent and antistain additive in an oral vehicle which typically includes water, it is highly preferred if not essential to add the additive after the other ingredients (except perhaps some of the water) are mixed or contacted with each other to avoid a tendency for said agent to be precipitated.

For instance, a mouthrinse or mouthwash may be prepared by mixing ethanol and water with flavoring oil, nonionic surfactant, humectant, cationic antibacterial antiplaque agent, such as benzethonium chloride or chlorohexidine, sweetener, color and then the above defined antistain additive, followed by additional water as desired.

A toothpaste may be prepared by forming a gel with humectant, gum or thickener such as hydroxyethyl cellulose, sweetener and adding thereto polishing agent, flavor, antibacterial agent, such as benzethonium chloride or chlorhexidine, additional water, and then the above-defined antistain additive. If sodium carboxymethyl cellulose is employed as the gelling agent, the procedure of either U.S. Pat. Nos. 3,842,168 or 3,843,779, modified by the inclusion of the additive, is followed.

In the practice of this invention an oral composition according to this invention such as a mouthwash or toothpaste containing cationic or long chain amine antibacterial antiplaque agent in an amount effective to promote oral hygiene and the defined additive in an amount effective to reduce staining of dental surfaces otherwise resulting from the presence of the antibacterial antiplaque agent, is applied regularly to dental enamel, preferably from about 5 times per week to about 3 times daily, at a pH of about 4.5 to about 9, generally about 5.5 to about 8, preferably about 6 to 8.

The following examples further exemplify the oral compositions of this invention and their advantages. Unless otherwise indicated all percent concentrations are in weight percent of the composition.

EXAMPLE 1

Two different mouthrinse formulations containing chlorhexidine gluconate and sodium azacycloheptane diphosphonate (AHP) were prepared for stability and pre-clinical evaluation. The mouthrinse formulae are listed in Table 1. To prepare the mouthrinses, the appropriate quantity of surfactant (PEG-40 sorbitan diisostearate or coco-amidopropyl betaine) and chlorhexidine gluconate were admixed in one-half ($\frac{1}{2}$) the rinse's volume of distilled water. With mixing, a solution of AHP was added slowly to the chlorhexidine/surfactant solution to yield a final rinse concentration of 0.59% sodium AHP (w/v). The pH of the mouthrinse was adjusted to a value of 7.0 with glacial acetic acid and the remaining ingredients were added at the concentrations shown in Table 1.

TABLE 1

| Ingredients Option | SAMPLE 1 Betaine Option (%) | SAMPLE 2 Nonionic (%) |
|---|---|---|
| Chlorhexidine gluconate (A.I.) | 0.12 | 0.12 |
| Coco-amidopropyl betaine (A.I.) | 0.25 | — |
| PEG Sorbitan diisostearate | — | 0.20 |
| Sod. AHP | 0.59 | 0.59 |
| Sod. saccharin | 0.01 | 0.01 |
| Glycerine | 10.00 | 10.00 |
| Ethanol | 10.00 | 10.00 |
| Flavor | 0.04 | 0.04 |
| pH | 7.00 | 7.00 |
| Water | QS 100.00 | QS 100.00 |

EXAMPLE 2

Nine week accelerated aging tests where conducted for the mouthrinses described in Example I. The concentration of chlorhexidine (CHX) was measured by the method of Gaffney and Cooke (J. Chromato.(1984) 306:303-313) whereas AHP was determined via Dionex chromatography. Table 2 illustrates the data obtained.

TABLE 2

| Mouthrinse | Temp (°C.) | Percent Recovery of Actives (%) CHX | AHP | Physical Appearance |
|---|---|---|---|---|
| CHX solution Control | 25 | 102 | — | clear solution |
|  | 49 | 105 | — | clear solution |
| AHP solution Control | 25 | — | 102 | clear solution |
|  | 49 | — | 107 | clear solution |
| Sample 1 (CHX/Betaine/AHP mouthrinse) | 25 | 101 | 100 | clear solution |
|  | 49 | 100 | 105 | clear solution |
| Sample 2 (CHX/Nonionic/AHP mouthrinse) | 25 | 108 | 92 | clear solution |
|  | 49 | 96 | 91 | clear solution |

The CHX solution control was a 0.12% CHX, by weight, aqueous solution. The AHP solution control was a 0.6% AHP, by weight, aqueous solution. After 9 weeks aging at 25° C. both mouthrinse formulations, samples 1 and 2 were optically clear and devoid of precipitation. The stability of the rinses stored at 49° C. were acceptable, although the nonionic option exhibited a trace of precipitation. To overcome this it is preferred that the concentration of PEG-40 sorbitan diisostearate be increased to 0.225%

EXAMPLE 3

The antiplaque activity of a chlorhexidine solution or mouthrinse was measured by an in vitro plaque assay. Extracted, non-carious human incisors were cleaned of gross deposits and polished with pumice using a dental drill. The root surface was removed at the cementoenamel junction and the enamel portion of the tooth was attached to nichrome wire with the aid of epoxy. Each tooth was suspended from a cap(10 dram vial) such that the tooth would be submerged when the vial contained 10 ml of liquid. The teeth were sterilized by irradiation with UV light for 2 hours. After sterilization, the teeth were treated for 30 seconds with the appropriate mouthrinse, washed extensively with Resting Saliva Salts Buffer(1.1 mM $CaCl_2$, 0.6 mM $KH_2PO_4$, 50 mM NaCl—pH 7.0), and aseptically transferred to vials containing 10 ml Trypticase Soy broth (Difco) with 3% sucrose which had been pre-inoculated to a high cell density with an 18 hours culture of Actinomyces viscous T14v and Streptococcus mutans JBP. After 24 hours of plaque development, the teeth were retreated with the test mouthrinses and then transferred to new vials pre-inoculated with bacteria. The treatment and plaque growth procedure was repeated for four successive days at which time plaque was removed from the teeth by exposing the teeth to sonic energy. Plaque was quantified by measuring the bacterial deoxyribonucleic acid(DNA) associated with each tooth according to the fluorescence DNA assay of Labarca and Paigen(Anal.-Biochem.(1980) 102:344-352). Table 3 summarizes the data obtained.

TABLE 3

| Rinse | N | Plaque DNA Recovered (ug/ tooth ± SD) | Percent Reduction (%) |
|---|---|---|---|
| Control (water) | 5 | 96 ± 13 | — |
| Commercial CHX Product | 5 | 35 ± 19 | 63 |
| CHX/Nonionic/AHP-Sample 2 | 5 | 17 ± 9 | 82 |
| CHX/0.25% Bet/AHP-Sample 1 | 5 | 13 ± 12 | 86 |

The data in Table 3 shows clearly that both chlorhexidine/AHP mouthrinses significantly($p < 0.05$) reduced the formation of in vitro plaque. Indeed, the mouthrinses containing AHP appear to exhibit greater antiplaque efficacy than a commercially available chlorhexidine product.

EXAMPLE 4

An in vitro assay was used to assess the staining potential of the chlorhexidine mouthrinses. Into a two ounce bottle was added the following: 1.0 gram hydroxyapatite beads, 1.25 ml 0.1 sodium phosphate buffer(pH 7.0), 5 ml 0.1M sodium phosphate buffer (pH 7.0) containing 2.5% Bovine Serum Albumine(Sigma Chemical Co., Type V), 12.5 ml test mouthrinse, and 6 ml 30% acetaldehyde prepared in 0.1M sodium phosphate buffer(pH 7.0). The mixture was shaken vigorously for 72 hours at 37° C. After this incubation, the solid was collected by filtration, washed with 10 ml 0.1M sodium phosphate buffer(pH 7.0), and dried for 24 hours at 37° C. The color retained to the hydroxyapatite was measured using a Gardner Reflectometer (Pacific Scientific, Silver Springs, MD) and is expressed as reflectance(RD) units (i.e. the lower the reflectance, the greater the stain). Table 4 summarizes the data obtained.

TABLE 4

| Mouthrinse | N | Mean Stain (Rd ± SD) | Relative Stain |
|---|---|---|---|
| Water Control | 4 | 52 ± 1 | 0 |
| Chlorhexidine Soln | 4 | 34 ± 1 | 100 |
| CHX/betaine/AHP | 4 | 43 ± 1 | 52 |
| CHX/nonionic/AHP | 4 | 46 ± 1 | 32 |

The data of Table 4 clearly illustrate the antistaining characteristics of the chlorhexine/AHP compositions.

EXAMPLE 5

An oral composition of this invention is prepared as a dentifrice having the formula shown in Table 5.

TABLE 5

| Ingredient | Percent (%) |
|---|---|
| Chlorhexidine gluconate (A.I) | 0.89 |
| Coco-amidopropyl betaine (A.I.) | 1.50 |
| Xylitol | 20.00 |
| Sodium Azacycloheptane Diphosphate | 1.00 |
| Sodium saccharin | 0.06 |
| Sodium Fluoride | 0.24 |
| Diatomaceous earth abrasive | 20.00 |
| Hydroxyethyl cellulose | 2.50 |
| Flavor | 1.00 |
| Water | QS to 100.00 |

This dentifrice exhibits anticalculus and antistain activity.

EXAMPLE 6

The plaque inhibiting characteristics of the AHP-containing compositions of this invention are illustrated by this Example. Ten subjects took part in a four day study during each phase of which, no other oral hygiene was employed (e.g. no tooth brushing or the like). The subjects were given a complete dental prophylaxis and entered each treatment phase of the study. Each subject rinsed for one minute, twice daily, with approximately 15 ml. of each treatment solution listed in Table 6. At the end of each treatment phase, plaque on all surfaces were scored according to the method of Silness and Loe (1964) Periodontal disease in Pregnancy, Acta. Odontol. Scad. 22:121-135. The placebo rinse treatment consisted of the solution of Sample 2 of Example 1 with the exception that it contained no CHX or AHP. The 0.12% CHX rinse treatment consisted of the solutions of Sample 2 of Example 1 with the exception that it contained no AHP. The CHX and AHP rinse treatment consisted of the solution of Sample 2 of Example 1.

TABLE 6

| Treatment | Mean Plaque Score | % Plaque Reduction |
|---|---|---|
| Placebo Rinse | 1.60 | 0 |
| CHX Rinse | 0.57 | 64 |
| CHX & AHP Rinse | 0.43 | 73 |

As can be seen, the CHX rinse as well as the stain reducing CHX and AHP rinse of this invention results in significant plaque reduction.

What is claimed is:

1. An oral composition which is a dentifrice, mouthrinse or toothpaste comprising: an oral vehicle having incorporated therein a non-ionic surfactant or an amphoteric betaine surfactant and free of anionic surfactant; about 0.01 to about 5.0% by weight of at least one nitrogen-containing cationic antibacterial, antiplaque agent which can stain or discolor dental surfaces; and, as an antistaining additive, 0.001 to about 10% by weight of an azacycloalkane diphosphonic acid or an orally acceptable salt thereof wherein said azacycloalkane diphosphonic acid is present in a quantity of about 0.1 to about ten times by weight of the staining antibacterial antiplaque agent, the quantity being sufficient to provide antistaining properties but insufficient to cause precipitation of the anti bacterial agent.

2. The oral composition of claim 1 wherein said staining antibacterial antiplaque agent is a substituted guanidine.

3. The oral composition of claim 1 wherein said staining antibacterial antiplaque agent is a pharmaceutically acceptable water soluble salt of an agent selected from the group consisting of chlorhexidine and alexidine.

4. The oral composition of claim 3 wherein said agent is chlorhexidine.

5. The oral composition of claim 1 wherein said staining, antibacterial, antiplaque agent is benzethonium chloride.

6. The oral composition of claim 1 wherein said staining antibacterial antiplaque agent is an antibacterial quaternary ammonium compound containing one to two alkyl groups of 8 to 20 carbon atoms.

7. The oral composition of claim 1 wherein said staining antibacterial antiplaque agent is cetyl pyridinium chloride.

8. The oral composition of claim 1 wherein said antistaining additive is azacycloheptane diphosphonic acid or an orally acceptable salt thereof.

9. A method for reducing the dental surface staining properties of an oral composition containing about 0.01 to about 5.0% by weight of at least one nitrogen containing antibacterial antiplaque agent which can stain or discolor said dental surfaces which method comprises including in said oral composition 0.001 to about 10% by weight of an azacycloalkane diphosphonic acid or an orally acceptable salt thereof, the azacycloalkane diphosphonic acid being present in a quantity of from about 0.1 to about ten times by weight of the staining antibacterial antiplaque agent, the quantity being sufficient to provide antistaining properties but insufficient to cause precipitation of the antibacterial agent.

10. The method of claim 9 wherein said staining antibacterial antiplaque agent is a substituted guanidine.

11. The method of claim 9 wherein said staining antibacterial antiplaque agent is a pharmaceutically acceptable water soluble salt of an agent selected from the group consisting of chlorhexidine and alexidine.

12. The method of claim 11 wherein said agent is chlorhexidine.

13. The method of claim 9 wherein said staining, antibacterial, antiplaque agent is benzethonium chloride.

14. The method of claim 9 wherein said staining antibacterial antiplaque agent is an antibacterial quaternary ammonium compound containing one to two alkyl groups of 8 to 20 carbon atoms.

15. The method of claim 9 wherein said staining antibacterial antiplaque agent is cetyl pyridinium chloride.

16. The method of claim 9 wherein said antistaining additive is azacycloheptane diphosphonic acid or an orally acceptable salt thereof.

* * * * *